United States Patent
Ayyat et al.

(10) Patent No.: US 12,243,648 B2
(45) Date of Patent: Mar. 4, 2025

(54) EVALUATION OF DONOR LUNGS DURING EX-VIVO LUNG PERFUSION

(71) Applicant: THE CLEVELAND CLINIC FOUNDATION, Cleveland, OH (US)

(72) Inventors: Kamal S. Ayyat, Cleveland, OH (US); Toshihiro Okamoto, Cleveland, OH (US); Kenneth R. McCurry, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 307 days.

(21) Appl. No.: 17/726,746

(22) Filed: Apr. 22, 2022

(65) Prior Publication Data

US 2022/0344056 A1 Oct. 27, 2022

Related U.S. Application Data

(60) Provisional application No. 63/178,190, filed on Apr. 22, 2021.

(51) Int. Cl.
| | | |
|---|---|---|
| *G06T 7/00* | (2017.01) | |
| *G16H 10/60* | (2018.01) | |
| *G16H 30/40* | (2018.01) | |
| *G16H 50/30* | (2018.01) | |

(52) U.S. Cl.
CPC .......... *G16H 50/30* (2018.01); *G06T 7/0012* (2013.01); *G16H 10/60* (2018.01); *G16H 30/40* (2018.01); *G06T 2200/24* (2013.01); *G06T 2207/10116* (2013.01); *G06T 2207/10132* (2013.01); *G06T 2207/20081* (2013.01); *G06T 2207/30061* (2013.01)

(58) Field of Classification Search
CPC ........ G16H 50/30; G16H 30/40; G16H 10/60; G06T 7/00; G06T 7/0012; G06T 2200/24; G06T 2207/10132; G06T 2207/30061; G06T 2207/10116; G06T 2207/20081
See application file for complete search history.

(56) References Cited

PUBLICATIONS

International Search Report for Corresponding Serial No. PCT/US2022/025892, Dated Aug. 1, 2022.

(Continued)

*Primary Examiner* — Tuan H Nguyen
(74) *Attorney, Agent, or Firm* — Tarolli, Sundheim, Covell & Tummino LLP (57) ABSTRACT

Systems and methods are provided for evaluating a donor lung undergoing ex-vivo perfusion. The system includes a processor and a non-transitory computer readable medium storing executable instructions. The executable instructions include a feature extractor that generates a plurality of parameters representing the donor lung undergoing ex-vivo perfusion. At least one of the plurality of parameters are ordinal categorical parameters that can assume one of a plurality of categorical values. A score calculator is configured to assign a numerical value to each of the ordinal categorical parameters according to the categorical value associated with the parameter and to determine a composite score representing a suitability of the donor lung undergoing ex-vivo perfusion for transplant from the plurality of parameters. A user interface is configured to provide an output representing the composite score to a user at an associated output device.

18 Claims, 3 Drawing Sheets

(56) References Cited

PUBLICATIONS

Ayyat, Kamal S., et al. "A CLUE for better assessment of donor lungs: Novel technique in clinical ex vivo lung perfusion." The Journal of Heart and Lung Transplantation 39.11 (2020): 1220-1227.
Okamoto, Toshihiro, et al. "Machine perfusion of lungs." Current Transplantation Reports 6.4 (2019): 251-264.
Divithotawela, Chandima, et al. "Long-term outcomes of lung transplant with ex vivo lung perfusion." JAMA surgery 154.12 (2019): 1143-1150.
Trebbia, Grégoire, et al. "Assessment of lung edema during ex-vivo lung perfusion by single transpulmonary thermodilution: A preliminary study in humans." The Journal of Heart and Lung Transplantation 38.1 (2019): 83-91.
Yeung, Jonathan C., et al. "Physiologic assessment of the ex vivo donor lung for transplantation." The Journal of Heart and Lung Transplantation 31.10 (2012): 1120-1126.
Cypel, Marcelo, et al. "Experience with the first 50 ex vivo lung perfusions in clinical transplantation." The Journal of thoracic and cardiovascular surgery 144.5 (2012): 1200-1207.
Sanchez, Pablo G., et al. "Defining quality during ex vivo lung perfusion: The University of Maryland experience." The Journal of thoracic and cardiovascular surgery 150.5 (2015): 1376-1377.
Ayyat, Kamal S., et al. "DireCt lung ultrasound evaluation (CLUE): a novel technique for monitoring extravascular lung water in donor lungs." The Journal of Heart and Lung Transplantation 38.7 (2019): 757-766.
Canadian Intellectual Property Office—Office Action dated Dec. 19, 2024, issued for Application No. 3,216,264, PCT No. US2022025892, 4 pages.

EVALUATION OF DONOR LUNGS DURING EX-VIVO LUNG PERFUSION

RELATED APPLICATIONS

This application claims priority to U.S. Provisional Patent Application Ser. No. 63/178,190 ("the '190 application"), filed Apr. 22, 2021 and entitled COMPLETE SCORE FOR EVALUATING DONOR LUNGS ON EVLP. The entirety of the '975 application is hereby incorporated by reference.

TECHNICAL FIELD

This disclosure relates to medical imaging and, more particularly, to evaluation of donor lungs during ex-vivo lung perfusion.

BACKGROUND

Lung content of extravascular lung water (EVLW) can significantly affect pulmonary functions. Multiple factors can play a role in changing the amount of EVLW like lung injury and hemodynamic status. Additionally, a marked heterogeneity is observed in the distribution of EVLW. It may vary across different areas in the same lung and being more susceptible to collapse and injury, lower lobes might have a higher content of EVLW. Quantification of EVLW in each part of the lungs is crucial for patient management.

Ex-vivo lung perfusion (EVLP) is a rapidly growing technology that has been adopted by many lung transplant (LTx) centers aiming to narrow the gap between supply and demand for donor lungs. Targeting marginal donor lungs, EVLP carries great potential for expanding donor lung pool, yet accurately judging lungs for transplant suitability during EVLP is crucial for maintaining satisfactory outcomes of LTx. Currently, the conventional tools utilized for assessing graft function during EVLP with an acellular perfusate remains insufficient.

SUMMARY

In one example, a system is provided for evaluating a donor lung undergoing ex-vivo perfusion. The system includes a processor and a non-transitory computer readable medium storing executable instructions. The executable instructions include a feature extractor configured to generate a plurality of parameters representing the donor lung undergoing ex-vivo perfusion. A set of at least one of the plurality of parameters are ordinal categorical parameters that can assume one of a plurality of categorical values. A score calculator is configured to assign a numerical value to each of the set of at least one of the plurality of parameters according to the categorical value associated with the parameter and to determine a composite score representing a suitability of the donor lung undergoing ex-vivo perfusion for transplant from the plurality of parameters. A user interface is configured to provide an output representing the composite score to a user at an associated output device.

In another example, a method is provided for evaluating a donor lung undergoing ex-vivo perfusion. The method includes generating a plurality of parameters representing the donor lung undergoing ex-vivo perfusion. A set of at least one of the plurality of parameters are ordinal categorical parameters that can assume one of a plurality of categorical values. A numerical value is assigned to each of the set of at least one of the plurality of parameters according to the categorical value associated with the parameter. A composite score representing a suitability of the donor lung undergoing ex-vivo perfusion for transplant is determined from the plurality of parameters. An output representing the composite score is provided to a user at an associated output device.

In yet another example, a method is provided for evaluating a donor lung undergoing ex-vivo perfusion. The method includes generating a plurality of parameters representing the donor lung undergoing ex-vivo perfusion. The plurality of parameters includes at least two of an initial weight of the donor lung, a direct lung ultrasound evaluation score, a final ratio of arterial oxygen partial pressure to fractional inspired oxygen for the donor lung, a final airway pressure for the donor lung, a parameter representing compliance of the donor lung, a final lactate level for the donor lung, a parameter representing deflation of the donor lung, a parameter representing palpation of the donor lung, a parameter representing secretions identified during bronchoscopy of the donor lung, and a level of infiltrations seen in an X-ray of the donor lung. A composite score representing a suitability of the donor lung undergoing ex-vivo perfusion for transplant is determined from the plurality of parameters. The composite score is compared to a threshold value, and the donor lung is transplanted into a patient only if the composite score meets the threshold value.

DETAILED DESCRIPTION

With absence of an oxygen carrier (e.g., hemoglobin) in acellular EVLP systems, gold standard parameters used in donor lung evaluation, like PaO2/FiO2 (P/F) ratio, seem to be useless in acellular EVLP setting. The amount of EVLW can change in donor lungs in a time-dependent fashion during the procurement process. For brain dead donors, the EVLW amount can be affected by the proinflammatory response, cardiac dysfunction, ventilator management, or fluid replacement during the donor management period. In the circumstance of donation after circulatory death, hypoxic pulmonary vasoconstriction and profound catecholamine surge occurring after withdrawal of life-sustaining therapy could dramatically change the EVLW content in donor lungs. Importantly, this type of change cannot be assessed accurately in vivo, however, it can adversely affect recipient outcome.

Previous studies have reported worse LTx outcomes post EVLP utilizing conventional methods of assessment, suggesting that parameters like partial pressure of oxygen (PO2), P/F ratio, static lung compliance, and pulmonary artery pressure can be misleading in acellular EVLP settings. On the other hand, centers with more EVLP experience have reported acceptable LTx outcomes post EVLP. This might be contributed to the main role played by the subjective evaluation in the current EVLP protocols. Additionally, the currently utilized cut off values for standard parameters has no scientific rational, which may have contributed to the significant differences in the outcomes of different EVLP programs outcomes.

The inventors propose the use of multiple numerical parameters in determining the suitability of a donor lung undergoing ex-vivo lung perfusion. The parameters used can include two or more of a direCt Lung Ultrasound Evaluation (CLUE), a lung weight measurement, a peak airway pressure, a dynamic lung compliance measure, a P/F ratio, a lactate level, a deflation test, a palpation measure, bronchoscopic findings, and a parameter derived from x-ray evaluation. In one implementation, at least one of the parameters is an ordinal parameter having a plurality of categorical values which can be arranged into a meaningful ranking. In another implementation, at least one parameter is a continuous or discrete parameters that is converted into an ordinal parameter according to a set of thresholds.

In one implementation, the parameters are each generated as or converted to an ordinal parameter and used to generate a composite score. Each parameter is assigned a category with an associated value varying from zero to three, with three being the category associated with unsuitability for transplant. The composite score is calculated by generating a linear combination of the individual parameter scores, and the generated linear combination is compared to a threshold value. Accumulated data, including the outcomes of lung transplantations, can be used for training a machine learning system or for determining appropriate threshold values for the composite score.

As used herein, a "categorical parameter" is a parameter that can take on any of at least three discrete values representing various categories. An "ordinal categorical parameter" is a categorical parameter in which the discrete values have a natural ranking. One example of an ordinal categorical parameter could be a parameter than can assume the values "good," "better," and "best."

As used herein, a "parameter representing the lung" can be a parameter associated with the condition of the donor or the lung prior to the initiation of ex-vivo lung perfusion or the condition of the lung during ex-vivo lung perfusion.

As used herein, a "direCt Lung Ultrasound Evaluation" score refers to a score generated using the methods indicated in U.S. Pat. No. 10,970,840, titled "Evaluation of Lungs Via Ultrasound" and hereby incorporated by reference, and more specifically, the score calculated in Eq. 1 of that patent.

Figure 1:
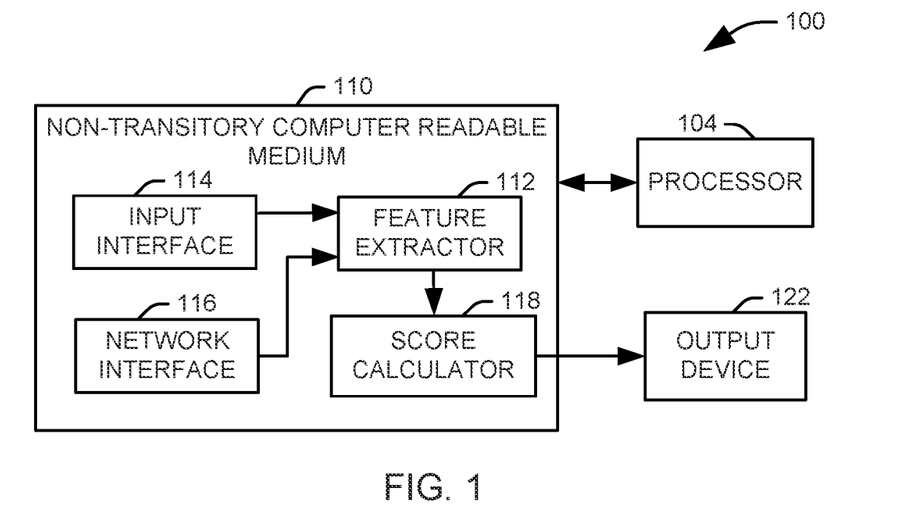
FIG. 1 illustrates a functional block diagram of an example of a system for evaluating a donor lung undergoing ex-vivo perfusion from one or more parameters representing the donor lung.

FIG. 1 illustrates a functional block diagram of an example of a system 100 for evaluating a donor lung undergoing ex-vivo perfusion from one or more parameters representing the donor lung and the donor providing the lung. The system 100 includes a processor 104 and a non-transitory computer readable medium 110 storing executable instructions for evaluating the donor lung. The executable instructions include a feature extractor 112 that generates a plurality of parameters representing the donor lung. In practice, the feature extractor 112 can receive any of medical data representing the donor, for example, via an electronic health records (EHR) database, imaging data representing the lung or the donor, data representing the opinion of a human expert on one or more parameters, and data from an independent expert system representing the lung or the donor and use this data to assign the plurality of parameters to the user. For example, numerical values can be retrieved from local or remote databases, received and buffered directly from one or more sensors or related systems, calculated from various properties of provided media, or extracted from structured, unstructured, or semi-structured text. In one implementation, the feature extractor 112 can receive data from either or both of an input interface 114 that receives data representing grades assigned by a human expert and a network interface 116 that allows the system to receive data from external sources, such as an EHR database or a repository of medical images associated with the lung or the donor. In practice, at least one of the plurality of parameters will be an ordinal categorical parameter representing the lung that can assume one of a plurality of categorical values.

In one example, the plurality of parameters includes at least two of an initial weight of the donor lung, a direct lung ultrasound evaluation score, a final ratio of arterial oxygen partial pressure to fractional inspired oxygen for the donor lung, a final airway pressure for the donor lung, a parameter representing compliance of the donor lung, a final lactate level for the donor lung, a parameter representing deflation of the donor lung, a parameter representing palpation of the donor lung, a parameter representing secretions identified during bronchoscopy of the donor lung, and a level of infiltrations seen in an X-ray of the donor lung. In other example, at least three of these parameters are used. In still another example, at least four of these parameters are used. In a further example, all ten of these parameters are used in evaluating the donor lung. It will be appreciated, however, that biometric parameters representing the donor and the lung in addition to these ten parameters can be extracted at the feature extractor 112.

A score calculator 118 assigns a numerical value to any ordinal categorical parameters according to the categorical value associated with the parameter and to determine a composite score representing a suitability of the donor lung undergoing ex-vivo perfusion for transplant from the plurality of parameters. In practice, each ordinal categorical parameter can have N possible values, which N is an integer greater than two, and each of the N possible values can have an associated numerical value that is assigned to the parameter to facilitate calculation of the score. In one example, each possible value is assigned a value ranging from zero to N−1 according to the ordinal ranking of the ordinal categorical parameter. In one example, values indicating that the donor lung is of poor quality can be larger values, with zero representing the value indicating good lung quality. In one example, any continuous parameters, for example, the final airway pressure for the donor, can be reduced to ordinal categorical parameters using a set of rules associated with each parameter. Once reduced to an ordinal categorical parameter, a numerical value representing the parameter can be assigned in the same manner as the native ordinal categorical parameters.

In one implementation, the score is generated as a linear combination of the values assigned to each parameter. In another implementation, the score calculator 118 provides the plurality of parameters to a machine learning model. The machine learning model can utilize one or more pattern recognition algorithms, implemented, for example, as classification and regression models, each of which analyze provided data to assign a clinical parameter to the user. It will be appreciated that the clinical parameter can be categorical or continuous. Where multiple classification and regression models are used, the machine learning model can include an arbitration element can be utilized to provide a coherent result from the various algorithms. Depending on the outputs of the various models, the arbitration element can simply select a class from a model having a highest confidence, select a plurality of classes from all models meeting a threshold confidence, select a class via a voting process among the models, or assign a numerical parameter based on the outputs of the multiple models. Alternatively, the arbitration element can itself be implemented as a classification model that receives the outputs of the other models as features and generates one or more output classes for the patient.

The machine learning model, as well as any constituent models, can be trained on training data representing the various classes of interest. For example, in supervised learning models, a set of examples having labels representing a desired output of the machine learning model can be used to train the system. The training process of the machine learning model will vary with its implementation, but training generally involves a statistical aggregation of training data into one or more parameters associated with the output classes. For rule-based models, such as decision trees, domain knowledge, for example, as provided by one or more human experts, can be used in place of or to supplement training data in selecting rules for classifying a user using the extracted features. Any of a variety of techniques can be utilized for the models, including support vector machines, regression models, self-organized maps, k-nearest neighbor classification or regression, fuzzy logic systems, data fusion processes, boosting and bagging methods, rule-based systems, or artificial neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. An SVM classifier utilizes a user-specified kernel function to organize training data within a defined feature space. In the most basic implementation, the kernel function can be a radial basis function, although the systems and methods described herein can utilize any of a number of linear or non-linear kernel functions.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

The classical ANN classifier is fully-connected and feed-forward. Convolutional neural networks, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feed-forward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A k-nearest neighbor model populates a feature space with labelled training samples, represented as feature vectors in the feature space. In a classifier model, the training samples are labelled with their associated class, and in a regression model, the training samples are labelled with a value for the dependent variable in the regression. When a new feature vector is provided, a distance metric between the new feature vector and at least a subset of the feature vectors representing the labelled training samples is generated. The labelled training samples are then ranked according to the distance of their feature vectors from the new feature vector, and a number, k, of training samples having the smallest distance from the new feature vector are selected as the nearest neighbors to the new feature vector.

In one example of a classifier model, the class represented by the most labelled training samples in the k nearest neighbors is selected as the class for the new feature vector. In another example, each of the nearest neighbors can be represented by a weight assigned according to their distance from the new feature vector, with the class having the largest aggregate weight assigned to the new feature vector. In a regression model, the dependent variable for the new feature vector can be assigned as the average (e.g., arithmetic mean) of the dependent variables for the k nearest neighbors. As with the classification, this average can be a weighted average using weights assigned according to the distance of the nearest neighbors from the new feature vector. It will be appreciated that k is a metaparameter of the model that is selected according to the specific implementation. The distance metric used to select the nearest neighbors can include a Euclidean distance, a Manhattan distance, or a Mahalanobis distance.

A regression model applies a set of weights to various functions of the extracted features, most commonly linear functions, to provide a continuous result. In general, regression features can be categorical, represented, for example, as zero or one, or continuous. In a logistic regression, the output of the model represents the log odds that the source of the extracted features is a member of a given class. In a binary classification task, these log odds can be used directly as a confidence value for class membership or converted via the logistic function to a probability of class membership given the extracted features.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used, but a continuous parameter can be computed according to a number of decision trees that select a given task. Regardless of the specific model employed, the composite score generated at the score calculator 118 can be provided to a user at the display 122 via a user interface or stored on the non-transitory computer readable medium 110, for example, in an electronic medical record associated with the patient. The score can then be used to evaluate the lung for transplant into a recipient. In one example, lungs having a score that meets a threshold value are considered suitable for transplant, and lungs having a score which fails to meet the threshold value are considered to be unsuitable for transport. Alternatively, the score can be used to rank donor lungs by suitability.

Figure 2:
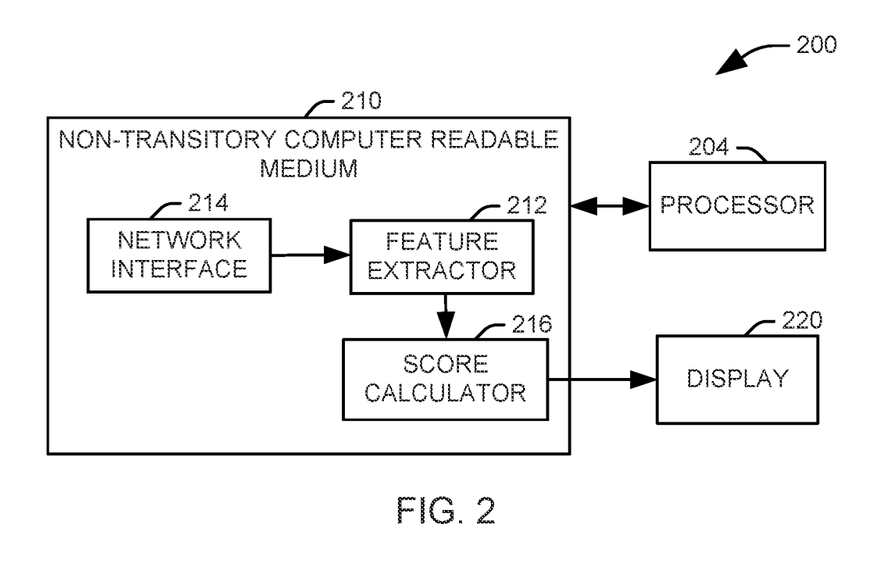
FIG. 2 illustrates a functional block diagram of another example of a system for evaluating a donor lung undergoing ex-vivo perfusion from one or more parameters representing the donor lung and the donor providing the lung.

FIG. 2 illustrates a functional block diagram of another example of a system 200 for evaluating a donor lung undergoing ex-vivo perfusion from one or more parameters representing the donor lung and the donor providing the lung. In the illustrated system 200, the one or more parameters used in evaluating the lung are initial weight of the donor lung, as a percentile of all donor lungs, a direct lung ultrasound (CLUE) evaluation score, a final ratio of arterial oxygen partial pressure to fractional inspired oxygen for the donor lung (P/F ratio), a final airway pressure for the donor lung (Ppeak) in cmH$_2$O, a parameter (C dyn) representing dynamic compliance of the donor lung in mL/cmH$_2$O, a final lactate level for the donor lung in mmol/L, a parameter representing deflation of the donor lung, a parameter representing palpation of the donor lung, a parameter representing secretions identified during bronchoscopy of the donor lung, and a level of infiltrations seen in an X-ray of the donor lung, as a percentage. Each of the deflation, palpation, and secretion parameters can be assigned by a human expert or determined by an expert system from imaging or other sensor data representing the lung.

The system 200 includes a processor 204 and a non-transitory computer readable medium 210 storing executable instructions for evaluating the donor lung. The executable instructions include a feature extractor 212 that generates the plurality of parameters representing the donor lung. In the illustrated implementation, the feature extractor 212 communicates with one or more other computer systems and devices via a network interface 214 to retrieve the data necessary to generate the plurality of features. It will be appreciated, however, that in some implementations, data can be entered directly via a user interface (not shown), received directly from an imaging device or sensor via a sensor interface (not shown), or retrieved from local storage.

Once a value has been generated for each of the ten parameters, a score calculator 216 converts each of the continuous parameters to ordinal categorical parameters according to sets of rules associated with each of the continuous parameters. In the illustrated implementation, each of the ordinal categorical parameters have four possible categories, or grades, and each of the continuous parameters can be assigned one of four possible categories, such that each of the ten parameters can assume one of four categorical values. Each category has an associated integer value between zero and three. The rules for assigning a value to each parameter, as well as the corresponding numerical value, are provided as Table 1.

TABLE 1

| Parameter\Grade | 0 | 1 | 2 | 3 |
|---|---|---|---|---|
| P/F | >400 | 300-400 | <300 in 2 differential ABG (arterial blood gas) | <300 in LA95 |
| Lung Weight (LW) | <50th percentile | 50th to 75th percentiles | 75th to 90th percentiles | >90th Or increase > 25 percentiles in final LW |
| CLUE | <0.8 | 0.8-1.3 | 1.4-1.7 | >1.7 |
| Ppeak | <12 | 12-14 | 15-17 | >17 Or Increase> 20% |
| C dyn | >80 | 67-80 | 55-66 | <55 Or Decline>20% |
| Lactate Level | <6 | 6-8 | 9-11 | >11 |
| Deflation Test | Complete All lobes | Incomplete in one lobes | No deflation in one lobe OR incomplete in 2 lobes | No deflation in > 2 lobes OR Incomplete in >2 lobes |
| Palpation | Normal in all lobes | Minimal Bogginess | Moderate Bogginess | Severe Bogginess |
| Bronchoscopy | No secretions | Minimal | Moderate | Severe |
| X-ray | No infiltrations | <25% | 25-50% | >50% |

The score calculator 216 then computes a composite score representing the suitability of the lung for transplant. In the illustrated system, larger values of the composite score indicate decreased suitability for transplant, although it will be appreciated that the values assigned to the various grades of the parameters could be reversed, such that larger scores corresponded to increased suitability for transplant. The composite score can then be compared to a threshold value to determine if the lung is suitable for transplant. Using the rules and scoring described in Table 1, a threshold value of twelve has been determined to distinguish between suitable and unsuitable lungs, with lungs above that value deemed unsuitable for transplant. The score and/or the determined suitability of the lung can be provided to the user at an associated display 220. The system 200 facilitates decision making in EVLP in a protocolized manner. It is a translation of years EVLP experience into a scoring system that provides an adequate, yet simple, way to judge donor lungs on EVLP for transplant suitability. The composite score has been found to be significantly higher in EVLP lungs deemed nonsuitable for transplant and, in those transplanted after EVLP, the score had a significant correlation with time to extubation, ICU stay, and incidence of primary graft dysfunction.

Figure 3:
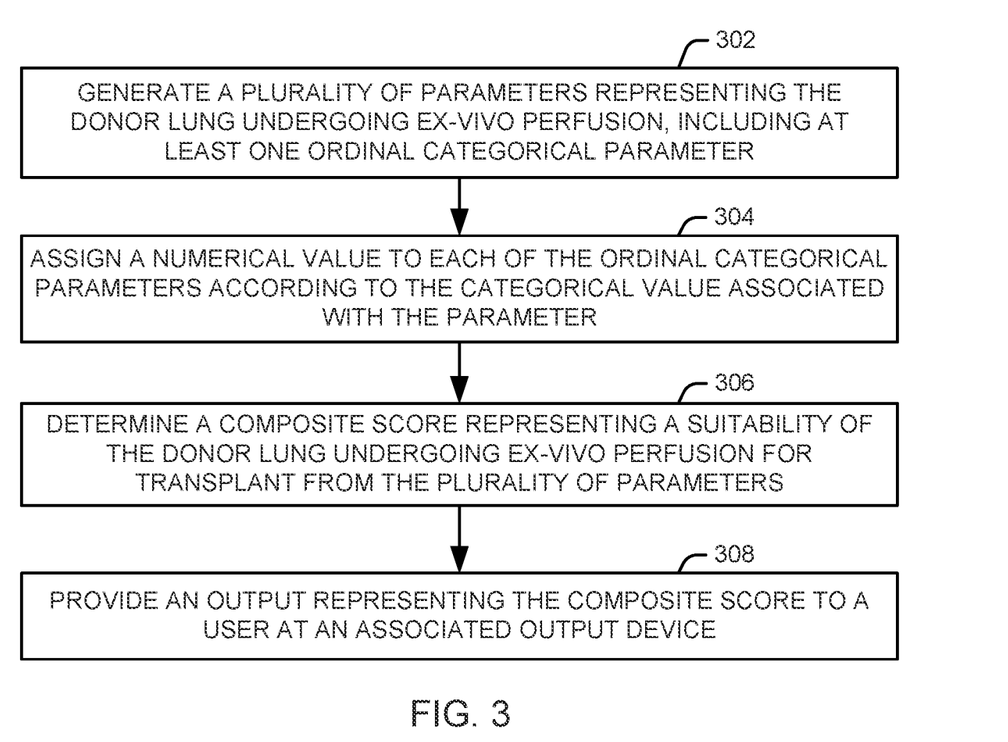
FIG. 3 illustrates one example of a method for evaluating a donor lung undergoing ex-vivo perfusion.
Figure 4:
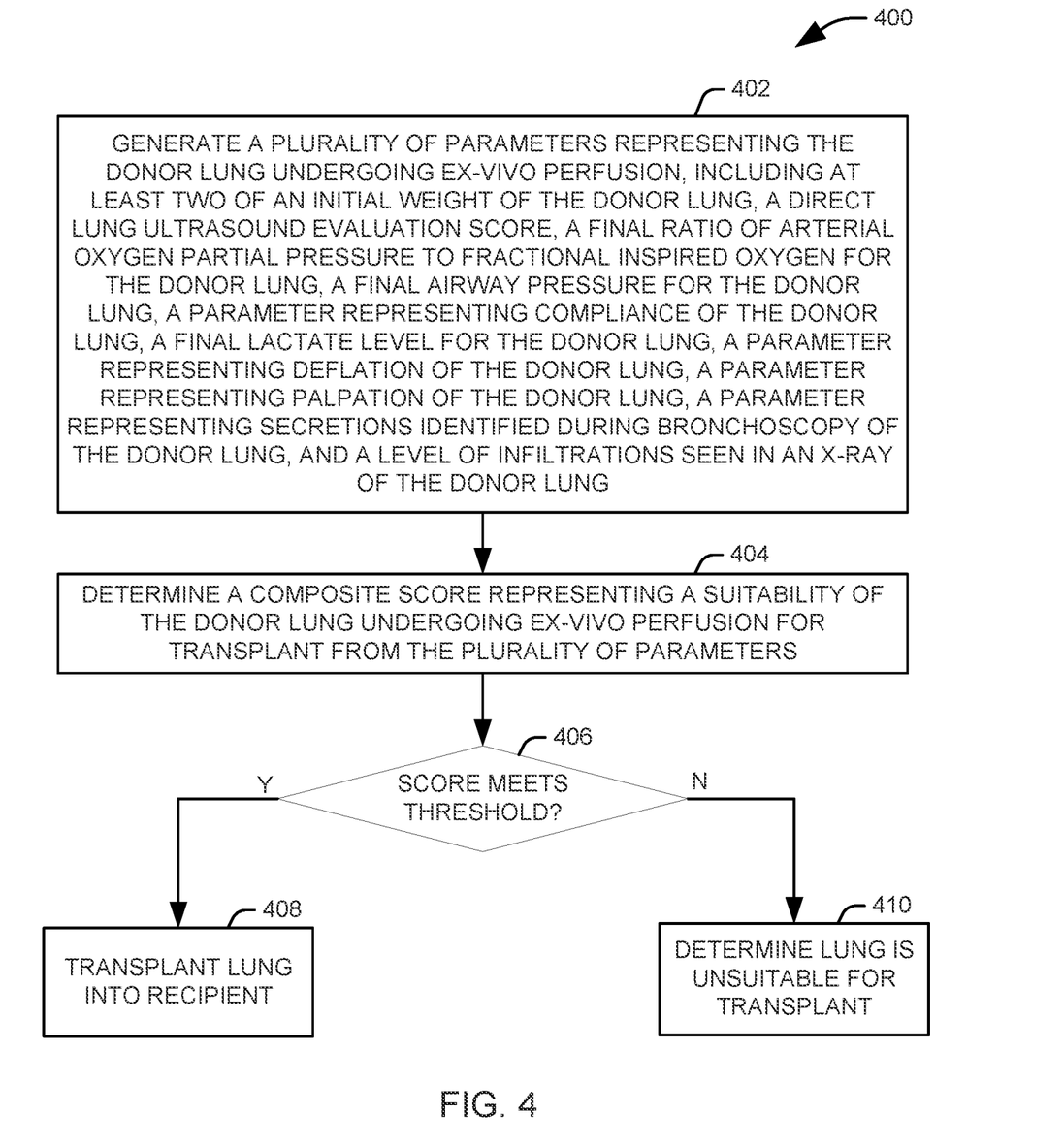
FIG. 4 illustrates another example of a method for evaluating a donor lung undergoing ex-vivo perfusion.

In view of the foregoing features described above, example methods will be better appreciated with reference to FIGS. 3 and 4. While, for purposes of simplicity of explanation, the method is shown and described as executing serially, it is to be understood and appreciated that the method is not limited by the illustrated order, as parts of the method could occur in different orders and/or concurrently from that shown and described herein.

FIG. 3 illustrates one example of a method 300 for evaluating a donor lung undergoing ex-vivo perfusion. At 302, a plurality of parameters representing the donor lung undergoing ex-vivo perfusion are generated. A set of at least one of the plurality of parameters are ordinal categorical parameters that can assume one of a plurality of categorical values. In one example, the plurality of parameters includes at least four of an initial weight of the donor lung, a direct lung ultrasound evaluation score, a final ratio of arterial oxygen partial pressure to fractional inspired oxygen for the donor lung, a final airway pressure for the donor lung, a parameter representing compliance of the donor lung, a final lactate level for the donor lung, a parameter representing deflation of the donor lung, a parameter representing palpation of the donor lung, a parameter representing secretions identified during bronchoscopy of the donor lung, and a level of infiltrations seen in an X-ray of the donor lung. In one example, an ultrasound image of the donor lung is generated, and at least one of the plurality of parameters are derived from the ultrasound image.

At 304, a numerical value is assigned to each of the set of at least one of the plurality of parameters according to the categorical value associated with the parameter. At 306, a composite score representing a suitability of the donor lung undergoing ex-vivo perfusion for transplant is determined from the plurality of parameters. In one implementation, the composite score is determined by providing the plurality of parameters, including any assigned numerical scores, to a machine learning model. In another implementation, the plurality of parameters includes a second set of at least one of the plurality of parameters that are each continuous parameters, and these parameters are assigning an ordinal categorical value according to a set of rules associated with to the parameter. A numerical value to each of these parameters according to the ordinal categorical value assigned to the parameter. In this implementation, the composite score is determined as a linear combination of the numerical values assigned to each of the plurality of parameters.

At 308, an output representing the composite score is provided to a user at an associated output device. The output can include one or more of the score itself, a categorical parameter representing the suitability of the lung for transplant, and any numerical values assigned to the plurality of parameters. In one implementation, the composite score is compared to a threshold value, and the donor lung is determined to be suitable for transplant if the composite score meets the threshold value.

FIG. 4 illustrates one example of a method 400 for evaluating a donor lung undergoing ex-vivo perfusion. At 402, a plurality of parameters representing the donor lung undergoing ex-vivo perfusion are generated. The plurality of parameters include at least two of an initial weight of the donor lung, a direct lung ultrasound evaluation score, a final ratio of arterial oxygen partial pressure to fractional inspired oxygen for the donor lung, a final airway pressure for the donor lung, a parameter representing compliance of the donor lung, a final lactate level for the donor lung, a parameter representing deflation of the donor lung, a parameter representing palpation of the donor lung, a parameter representing secretions identified during bronchoscopy of the donor lung, and a level of infiltrations seen in an X-ray of the donor lung. In one example, one or more of these parameters can be determined by retrieving at least one of the plurality of parameters from an electronic health records database. In one implementation, a set of at least one of the plurality of parameters are ordinal categorical parameters that can assume one of a plurality of categorical values, and a numerical value is assigned to each of the set of at least one of the plurality of parameters according to the categorical value associated with the parameter.

At 404, a composite score representing a suitability of the donor lung undergoing ex-vivo perfusion for transplant is determined from the plurality of parameters. In one example, the plurality of parameters are provided to a machine learning model to provide the composite score. In another implementation, the composite score is determined as a linear combination of the numerical values associated with each of the plurality of parameters. In one example, the composite score can be provided to a user at an associated output device, such as a display. At 406, the composite score is compared to a threshold value. If the composite score meets the threshold value (Y), the method advances to 408, where the donor lung is transplanted into a patient. If the composite score does not meet the threshold value (N), the lung is determined to be unsuitable for transplant at 410.

Figure 5:
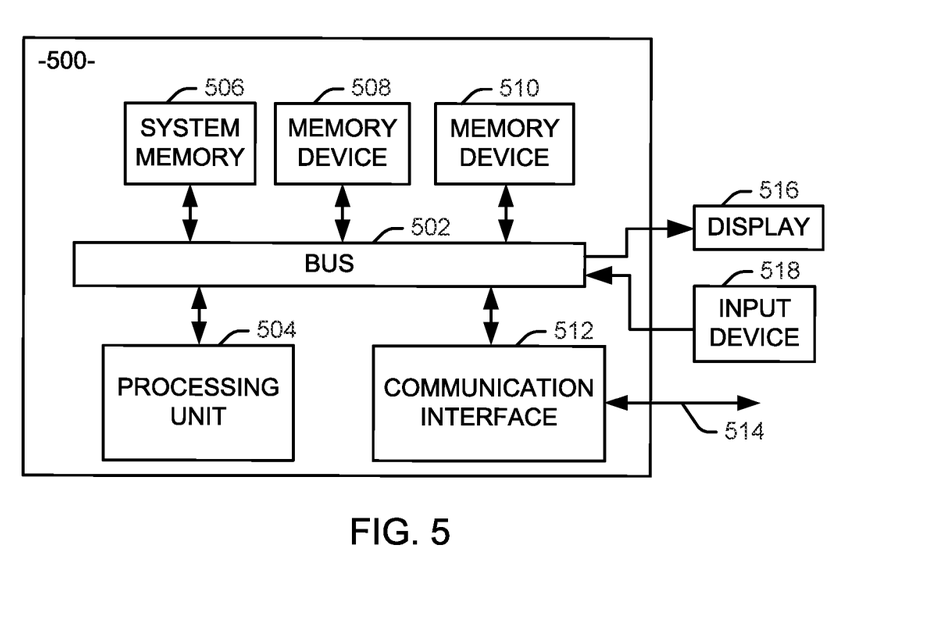
FIG. 5 is a schematic block diagram illustrating an exemplary system of hardware components capable of implementing examples of the systems and methods disclosed in FIGS. 1-4.

FIG. 5 is a schematic block diagram illustrating an exemplary system 500 of hardware components capable of implementing examples of the systems and methods disclosed herein. The system 500 can include various systems and subsystems. The system 500 can be a personal computer, a laptop computer, a workstation, a computer system, an appliance, an application-specific integrated circuit (ASIC), a server, a server BladeCenter, a server farm, etc.

The system 500 can include a system bus 502, a processing unit 504, a system memory 506, memory devices 508 and 510, a communication interface 512 (e.g., a network interface), a communication link 514, a display 516 (e.g., a video screen), and an input device 518 (e.g., a keyboard, touch screen, and/or a mouse). The system bus 502 can be in communication with the processing unit 504 and the system memory 506. The additional memory devices 508 and 510, such as a hard disk drive, server, standalone database, or other non-volatile memory, can also be in communication with the system bus 502. The system bus 502 interconnects the processing unit 504, the memory devices 506-510, the communication interface 512, the display 516, and the input device 518. In some examples, the system bus 502 also interconnects an additional port (not shown), such as a universal serial bus (USB) port.

The processing unit 504 can be a computing device and can include an application-specific integrated circuit (ASIC). The processing unit 504 executes a set of instructions to implement the operations of examples disclosed herein. The processing unit can include a processing core.

The additional memory devices 506, 508, and 510 can store data, programs, instructions, database queries in text or compiled form, and any other information that may be needed to operate a computer. The memories 506, 508 and 510 can be implemented as computer-readable media (integrated or removable), such as a memory card, disk drive, compact disk (CD), or server accessible over a network. In certain examples, the memories 506, 508 and 510 can comprise text, images, video, and/or audio, portions of which can be available in formats comprehensible to human beings. Additionally or alternatively, the system 500 can access an external data source or query source through the communication interface 512, which can communicate with the system bus 502 and the communication link 514.

In operation, the system 500 can be used to implement one or more parts of a system, such as that illustrated in FIG. 1. Computer executable logic for implementing the system resides on one or more of the system memory 506, and the memory devices 508 and 510 in accordance with certain examples. The processing unit 504 executes one or more computer executable instructions originating from the system memory 506 and the memory devices 508 and 510. The term "computer readable medium" as used herein refers to a medium that participates in providing instructions to the processing unit 504 for execution. This medium may be distributed across multiple discrete assemblies all operatively connected to a common processor or set of related processors.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system for evaluating a donor lung undergoing ex-vivo perfusion, the system comprising:
   a processor; and
   a non-transitory computer readable medium storing executable instructions, the executable instructions comprising:
     a feature extractor configured to generate a plurality of parameters representing the donor lung undergoing ex-vivo perfusion, wherein a first set of at least one of the plurality of parameters are ordinal categorical parameters that can assume one of a plurality of categorical values and a second set of at least one of the plurality of parameters are each continuous parameters;
     a score calculator configured to apply, for each of the second set of at least one of the plurality of parameters, a set of rules associated with the parameter to assign an ordinal categorical value from a plurality of ordinal categorical values to the parameter, assign a numerical value to each of the first set of at least one of the plurality of parameters and each of the second set of at least one of the plurality of parameters according to the categorical value associated with the parameter, and determine a composite score representing a suitability of the donor lung undergoing ex-vivo perfusion for transplant from the plurality of parameters; and
     a user interface configured to provide an output representing the composite score to a user at an associated output device.

2. The system of claim 1, wherein the feature extractor comprises an input interface for receiving data from a human expert representing at least one of the plurality of parameters.

3. The system of claim 1, wherein the feature extractor comprises a network interface for receiving data from an electronic health records system representing at least one of the plurality of parameters.

4. The system of claim 1, wherein the plurality of parameters consists of the first set of at least one of the plurality of parameters and the second set of at least one of the plurality of parameters, and the score calculator determines the composite score as a linear combination of the numerical values assigned to each of the plurality of parameters.

5. The system of claim 4, wherein there are N ordinal categorical values in the plurality of ordinal categorical values associated with each of the second set of at least one of the plurality of parameters and N categorical values in the plurality of categorical values associated with each of the first set of at least one of the plurality of parameters, wherein N is an integer greater than two, and the numerical value assigned to each of the plurality of parameters is an integer value ranging from zero to N−1.

6. The system of claim 1, the score calculator comprising a machine learning model configured to determine the composite score from the plurality of parameters.

7. The system of claim 1, wherein the plurality of parameters includes at least three of an initial weight of the donor lung, a direct lung ultrasound evaluation score, a final ratio of arterial oxygen partial pressure to fractional inspired oxygen for the donor lung, a final airway pressure for the donor lung, a parameter representing compliance of the donor lung, a final lactate level for the donor lung, a parameter representing deflation of the donor lung, a parameter representing palpation of the donor lung, a parameter representing secretions identified during bronchoscopy of the donor lung, and a level of infiltrations seen in an X-ray of the donor lung.

8. A method for evaluating a donor lung undergoing ex-vivo perfusion, the method comprising:
generating a plurality of parameters representing the donor lung undergoing ex-vivo perfusion, wherein a first set of at least one of the plurality of parameters are ordinal categorical parameters that can assume one of a plurality of categorical values and a second set of at least one of the plurality of parameters that are each continuous parameters;
assigning an ordinal categorical value from a plurality of ordinal categorical values to each of the second set of at least one of the plurality of parameters according to a set of rules associated with to the parameter;
assigning a numerical value to each of the first set of at least one of the plurality of parameters and the second set of at least one of the plurality of parameters according to the ordinal categorical value associated with the parameter;
determining a composite score representing a suitability of the donor lung undergoing ex-vivo perfusion for transplant from the plurality of parameters; and
providing an output representing the composite score to a user at an associated output device.

9. The method of claim 8, further comprising:
comparing the composite score to a threshold value; and determining that the donor lung is suitable for transplant if the composite score is meets the threshold value.

10. The method of claim 8, wherein determining the composite score comprises providing the plurality of parameters to a machine learning model.

11. The method of claim 8, wherein determining the composite score comprises determining the composite score as a linear combination of the numerical values assigned to each of the first set of at least one of the plurality of parameters and to the second set of at least one of the plurality of parameters.

12. The method of claim 8, wherein the plurality of parameters includes at least four of an initial weight of the donor lung, a direct lung ultrasound evaluation score, a final ratio of arterial oxygen partial pressure to fractional inspired oxygen for the donor lung, a final airway pressure for the donor lung, a parameter representing compliance of the donor lung, a final lactate level for the donor lung, a parameter representing deflation of the donor lung, a parameter representing palpation of the donor lung, a parameter representing secretions identified during bronchoscopy of the donor lung, and a level of infiltrations seen in an X-ray of the donor lung.

13. The method of claim 8, further comprising generating an ultrasound image of the donor lung, at least one of the plurality of parameters being derived from the ultrasound image.

14. A method for evaluating a donor lung undergoing ex-vivo perfusion, the method comprising:
generating a plurality of parameters representing the donor lung undergoing ex-vivo perfusion, the plurality of parameters including at least one of an initial weight of the donor lung, a direct lung ultrasound evaluation score, a final ratio of arterial oxygen partial pressure to fractional inspired oxygen for the donor lung, a final airway pressure for the donor lung, and a final lactate level for the donor lung, and at least one of a parameter representing compliance of the donor lung, a parameter representing deflation of the donor lung, a parameter representing palpation of the donor lung, a parameter representing secretions identified during bronchoscopy of the donor lung, and a level of infiltrations seen in an X-ray of the donor lung;
assigning an ordinal categorical value from a plurality of ordinal categorical values to the one of the initial weight of the donor lung, a direct lung ultrasound evaluation score, the final ratio of arterial oxygen partial pressure to fractional inspired oxygen for the donor lung, the final airway pressure for the donor lung, and the final lactate level for the donor lung according to a set of rules associated with to the parameter;
determining a composite score representing a suitability of the donor lung undergoing ex-vivo perfusion for transplant from the one of the parameter representing compliance of the donor lung, the parameter representing deflation of the donor lung, a parameter representing palpation of the donor lung, a parameter representing secretions identified during bronchoscopy of the donor lung, and a level of infiltrations seen in an X-ray of the donor lung and the ordinal categorical value assigned to the one of the initial weight of the donor lung, a direct lung ultrasound evaluation score, the final ratio of arterial oxygen partial pressure to fractional inspired oxygen for the donor lung, the final airway pressure for the donor lung, and the final lactate level for the donor lung;
comparing the composite score to a threshold value; and transplanting the donor lung into a patient only if the composite score meets the threshold value.

15. The method of claim 14, wherein a set of at least one of the plurality of parameters are ordinal categorical parameters that can assume one of a plurality of categorical values, the method further comprising assigning a numerical value to each of the set of at least one of the plurality of parameters according to the categorical value associated with the parameter.

16. The method of claim 14, further comprising providing an output representing the composite score to a user at an associated output device.

17. The method of claim 14, wherein determining the composite score comprises determining the composite score as a linear combination of the numerical values associated with each of the plurality of parameters.

18. The method of claim 14, wherein generating the plurality of parameters comprising retrieving at least one of the plurality of parameters from an electronic health records database.

* * * * *